(12) United States Patent
Sugiyama

(10) Patent No.: US 7,781,085 B2
(45) Date of Patent: Aug. 24, 2010

(54) MONOMER COMPOUND, GRAFT COPOLYMER COMPOUND, PRODUCTION METHOD THEREOF, POLYMER ELECTROLYTE MEMBRANE, AND FUEL CELL

(75) Inventor: Yuichiro Sugiyama, Chicago, IL (US)

(73) Assignee: Toyota Jidosha Kabushiki Kaisha, Tokyo (JP)

( * ) Notice: Subject to any disclaimer, the term of this patent is extended or adjusted under 35 U.S.C. 154(b) by 1110 days.

(21) Appl. No.: 10/566,187

(22) PCT Filed: Nov. 26, 2004

(86) PCT No.: PCT/JP2004/017988

§ 371 (c)(1),
(2), (4) Date: Apr. 10, 2006

(87) PCT Pub. No.: WO2005/051899

PCT Pub. Date: Jun. 9, 2005

(65) Prior Publication Data

US 2006/0286424 A1    Dec. 21, 2006

(30) Foreign Application Priority Data

Nov. 28, 2003  (JP) .............................. 2003-400060

(51) Int. Cl.
*H01M 8/10* (2006.01)
(52) U.S. Cl. ........................ 429/33; 521/27; 526/243; 528/401; 568/27
(58) Field of Classification Search .................. 429/33; 521/27; 528/401; 526/243; 568/27
See application file for complete search history.

(56) References Cited

U.S. PATENT DOCUMENTS

| 3,179,640 | A * | 4/1965 | Middleton ................. 526/249 |
| 6,359,019 | B1 * | 3/2002 | Stone et al. ................. 521/27 |
| 6,607,856 | B2 * | 8/2003 | Suzuki et al. ............... 429/30 |
| 2004/0116617 | A1 | 6/2004 | Ishihara et al. |
| 2006/0286424 | A1 * | 12/2006 | Sugiyama ................... 429/33 |
| 2007/0292734 | A1 * | 12/2007 | Kiefer et al. ............... 429/33 |

FOREIGN PATENT DOCUMENTS

| EP | 1 375 532 A1 | 1/2004 |
| EP | 1375532 A1 * | 1/2004 |
| JP | A-07-090111 | 4/1995 |
| JP | A-2001-021637 | 1/2001 |
| JP | A-2001-302721 | 10/2001 |
| JP | 2003-272665 * | 9/2003 |
| JP | A-2003-272665 | 9/2003 |
| WO | WO-2005/051899 A2 * | 6/2005 |

OTHER PUBLICATIONS

Ishihara et al., Angew. Chem., vol. 113 (21), pp. 4201-4203 (2001).*
Ishihara et al.; "Polystyrene-Bound Tetrafluorophenylbis(triflyl)methane as an Organic-Solvent-Swellable and Strong Bronsted Acid Catalyst"; Angewandte Chemie; vol. 113, No. 21 ; Nov. 5, 2001 ; pp. 4201-4203.*
Sprague et al.; "The Synthesis and Attempted Polymerization of an alpha, beta,beta-Trifluorostyrene Disubstituted by Hexafluoro-2-propanol Groups", Journal of Fluorine Chemistry, vol. 52, pp. 301-306, (1991).*
Ishihara et al.; "Polystyrene-Bound Tetrafluorophenylbis(triflyl)methane as an Organic-Solvent-Swellable and Strong Brønsted Acid Catalyst"; *Angewandte Chemie*; vol. 113, No. 21; Nov. 5, 2001; pp. 4201-4203.
Eisman; "The Application of Dow Chemical's Perfluorinated Membranes in Proton-Exchange Membrane Fuel Cells"; *Journal of Power Sources*; vol. 29; 1990; pp. 389-398.

* cited by examiner

*Primary Examiner*—Peter D. Mulcahy
*Assistant Examiner*—Henry Hu
(74) *Attorney, Agent, or Firm*—Oliff & Berridge, PLC

REACTION STEP (1)    REACTION STEP (2)

(57) ABSTRACT

A novel polymer electrolyte is provided that enables a solid polymer electrolyte used in fuel cells, for example, to have sufficient proton conductivity even in a low-water-content state or a zero-water-content state by using a monomer compound represented by the general formula (1), and a graft copolymer compound in which the monomer compound represented by the general formula (1) is graft-copolymerized to the main chain of a fluorine-containing hydrocarbon polymer.

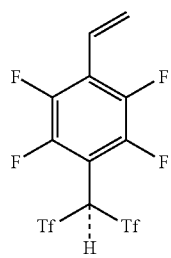

(1)

-continued

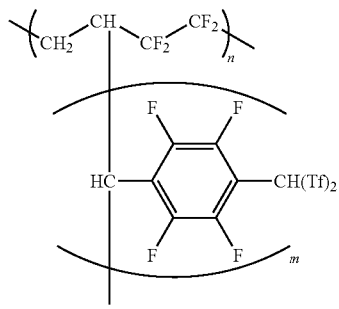

(2)

Tf indicates a trifluoromethane sulfonyl group ($-SO_2CF_3$).

3 Claims, 1 Drawing Sheet

MONOMER COMPOUND, GRAFT COPOLYMER COMPOUND, PRODUCTION METHOD THEREOF, POLYMER ELECTROLYTE MEMBRANE, AND FUEL CELL

TECHNICAL FIELD

The present invention relates to a monomer compound comprising a super strong-acidic group, a graft copolymer compound comprising the monomer compound, a production method thereof, a polymer electrolyte membrane comprising a super strong-acidic group, and a polymer electrolyte fuel cell comprising the polymer electrolyte membrane as a solid polymer electrolyte membrane.

BACKGROUND ART

Fuel cells are devices for gaining electric energy by an operational principle based upon reverse action of electrolysis of water. In general, hydrogen gained by transforming fuel such as natural gas, methanol, and coal, and oxygen in the air are supplied to the fuel cells in order to obtain direct-current power while generating water. Because the fuel cells have a high efficiency of electric power generation and are capable of supplying clean energy, fuel cell power generation has attracted attention.

The fuel cells are classified into a phosphoric acid type, a molten carbonate type, a solid oxide type, and a solid polymer type, for example, depending on the type of electrolyte used. In particular, polymer electrolyte fuel cells in which an ion exchange membrane (solid polymer electrolyte membrane) is used as an electrolyte are advantageous in that they are substantially exclusively composed of solid cells and are therefore not subject to the problem of scattering of the electrolytes or the maintenance thereof, the fuel cells can operate at low temperatures of not more than 100° C., the start-up time is extremely brief, and they are capable of achieving high energy density and reduction in size and weight, for example.

Therefore, polymer electrolyte fuel cells are being developed as power sources for automobiles, dispersed-type power sources for homes and buildings, power sources for space vehicles, and portable power sources. Specifically, in terms of environmental issues such as global warming and measures to reduce exhaust gas of automobiles, polymer electrolyte fuel cells are gaining attention as fuel cells to be used for automobiles.

Solid polymer electrolytes constitute a solid polymer material having an electrolyte group such as a sulfonic group in a polymer chain. As the solid polymer electrolytes have the property to strongly bind to specific ions and to allow positive or negative ions to be selectively transmitted, they are formed as particles, fibers, or membranes and are used for various applications such as electrodialysis, diffusion dialysis, and battery diaphragms.

For example, a polymer electrolyte fuel cell comprises a proton-conductive solid polymer electrolyte membrane with a pair of electrodes provided with one electrode on each side thereof. Hydrogen gas gained by reforming low molecular weight hydrocarbon such as methane and methanol is supplied to one of the electrodes (fuel electrode) as fuel gas, and oxygen gas or air is supplied to the other electrode (air electrode) as an oxidant in order to obtain an electromotive force. Water electrolysis is a method for producing hydrogen and oxygen by electrolyzing water using a solid polymer electrolyte membrane.

In consideration of the application of the polymer electrolyte fuel cells to electric automobiles, it is desired that the operation temperature of a fuel cell system be not less than 100° C. for downsizing the cooling system and improving the CO tolerance and the efficiency of the electrode catalyst. At such high temperatures, the vapor pressure of water increases, so that if the internal pressure of the batteries is to exist at a realistic level, the relative humidity of ambient atmosphere declines, making it necessary for the electrolyte membrane to have a sufficient proton conductivity in a low humidity environment.

In addition, although there is a demand that humidification from the outside using pure water be eliminated in order to simplify the system and avoid the problem of freezing in winter, if humidification is eliminated, it would require the ambient atmosphere inside the fuel cells to be maintained in a humid state using only generated water, resulting in low humidity environment likewise.

However, in general, the polymer electrolyte fuel cells are usually operated at a temperature of not more than 100° C. This is because perfluoro electrolyte membranes such as Nafion (registered trademark of DuPont) gains proton conductivity by containing water. Therefore, the water content of the membrane (the water content relative to the weight of dried membrane) is an extremely important factor. The membrane must be maintained in a sufficiently water-containing state if it is to produce proton conductivity, so that water control is required. Consequently, in general, reactant gas must be humidified when operating the batteries. However, humidification of the membrane becomes insufficient at high temperatures of not less than 100° C., so that the proton conductivity declines.

Also, the perfluoro electrolyte membranes are difficult to manufacture, and are highly expensive. This makes it difficult to apply the perfluoro electrolyte membranes to consumer use such as polymer electrolyte fuel cells as low-pollution power sources for automobiles As mentioned above, perfluoro electrolyte membranes such as Nafion cannot maintain strength at high temperatures or sufficient conductivity in a high temperature and low humidity environment, so that it is difficult to operate fuel cells in high temperature and low humidity conditions. Moreover, the cost is inevitably high.

In order to realize a fuel cell system capable of stable operation under such conditions as high temperature or a lack of humidification, it is extremely important to realize an electrolyte that exhibits conductivity in a low humidity environment. However, there has been no electrolyte having a high ion-exchange capacity and capable of a high degree of dissociation in a low humidity environment while providing a practical strength, and exhibiting sufficient proton conductivity in a high temperature and low humidity environment.

JP Patent Publication (Kokai) No. 7-90111 A (1995) 1 discloses an invention in which a metal catalyst and metal oxide are included in an electrolyte membrane in order to provide a polymer solid electrolyte composition having oxidation resistance equal to or greater than that of a fluorine electrolyte, or sufficient in practical use, which is superior in ion conductivity and the effect of crossover inhibition by having the ability of self generation and retainment of water, and which is most suitable as a membrane for an electrochemical cell such as a polymer solid electrolyte fuel cell. Specifically, at least one metal catalyst selected from the group consisting of platinum, gold, palladium, rubidium, iridium, and ruthenium is included in a polymer solid electrolyte selected from the group consisting of cation exchange resins and/or anion exchange resins, and microscopic particles and/or fibers of metal oxide such as silica and titania are further included.

DISCLOSURE OF THE INVENTION

In the invention disclosed in JP Patent Publication (Kokai) No. 7-90111 A (1995), in which the metal catalyst and metal oxide are included in the electrolyte membrane, membrane functions such as the proton conductivity decline since substances that are essentially unnecessary in terms of the membrane functions are added. This is caused by maintaining the humidity using additives.

In view of such problems as mentioned above, it is an object of the present invention to obtain a novel polymer electrolyte for fuel cells, for example, having a sufficient proton conductivity even in a low-water-content state or zero-water-content state. Also, the present invention provides a polymer electrolyte fuel cell comprising a polymer electrolyte membrane having such superior characteristics.

The inventors of the invention, as a result of extensive research, arrived at the present invention by solving the aforementioned problems using a graft copolymer compound comprising a monomer compound of specific structure in a graft chain thereof, the monomer compound having a super strong-acidic group.

In a first aspect, the present invention is an invention of a monomer compound, which is represented by the following general formula (1).

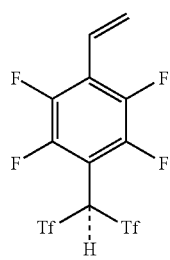
(1)

The monomer compound of the present invention comprises Tf (trifluoromethane sulfonyl group ($-SO_2CF_3$)), which is a super strong-acidic group.

In a second aspect, the present invention is an invention of a graft copolymer compound comprising a super strong-acidic group, in which the monomer compound represented by the aforementioned general formula (1) is graft-copolymerized to the main chain of a fluorine-containing hydrocarbon polymer. The main chain of a fluorine-containing hydrocarbon polymer is preferably an ethylene-tetrafluoroethylene copolymer, for example. The graft copolymer compound is represented by the following general formula (2). Tf indicates a trifluoromethane sulfonyl group ($-SO_2CF_3$).

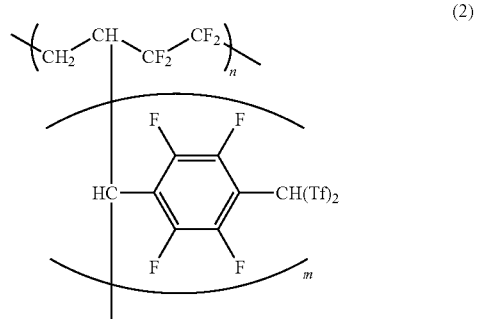

In a third aspect, the present invention is an invention of a method for manufacturing a graft copolymer compound, the method comprising causing the monomer compound represented by the aforementioned general formula (1) to be graft-copolymerized to a fluorine-containing hydrocarbon polymer.

In a fourth aspect, the present invention is an invention of a polymer electrolyte membrane obtained by processing the aforementioned graft copolymer compound. The invention also provides a polymer electrolyte membrane in which the monomer compound represented by the aforementioned general formula (1) is graft-copolymerized to a base film comprising a fluorine-containing hydrocarbon polymer. The polymer electrolyte membrane according to the present invention shows a sufficient proton conductivity even in a low-water-content state or zero-water-content state.

In a fifth aspect, the present invention is an invention of a polymer electrolyte fuel cell comprising the aforementioned electrolyte membrane, reactive poles that sandwich the electrolyte membrane, and separators that sandwich the reactive electrodes.

By using the monomer compound comprising a super strong-acidic group as mentioned above, a polymer electrolyte membrane can be obtained showing a sufficient proton conductivity even in a low-water-content state or zero-water-content state, without using additives unnecessary for the membrane components. By using the polymer electrolyte membrane in a fuel cell, the system operation temperature can be increased and a humidifier can be eliminated. As a result, the fuel cell system can be reduced in size, the CO tolerance of electrocatalyst can be improved, and freeze can be prevented, for example.

BEST MODE FOR CARRYING-OUT OF THE INVENTION

Figure 1:
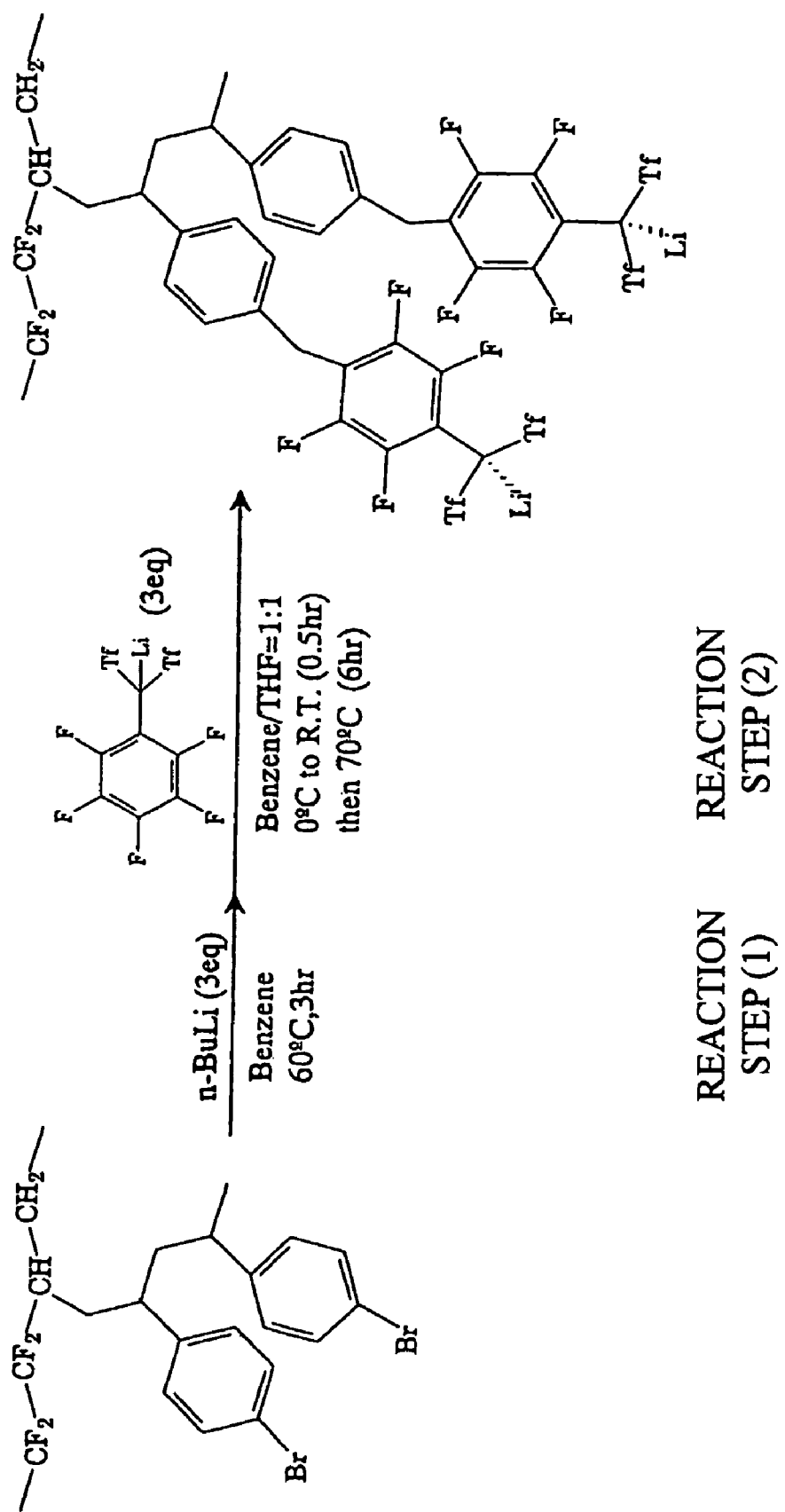
FIG. 1 shows an introduction scheme of a super strong-acidic group by a comparative example (conventional method).

In the following, the details of carrying out the embodiments of the present invention are described.

A monomer compound comprising a super strong-acidic group represented by the aforementioned general formula (1) is synthesized in the following scheme, for example.

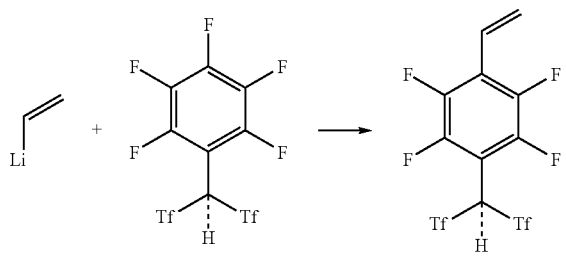

Examples of a fluorine-containing hydrocarbon polymer which constitutes the main chain of a graft copolymer compound comprising a super strong-acidic group according to the present invention include ethylene-tetrafluoroethylene copolymer, polytetrafluoroethylene, polyvinylidene fluoride, and hexafluoropropylene-tetrafluoroethylene copolymer, for example.

The manner of graft copolymerization is not especially limited. For example, a monomer compound represented by the aforementioned general formula (1), which constitutes a side chain, is graft-copolymerized in the presence of the fluorine-containing hydrocarbon polymer, which becomes the main chain, using thermopolymerization, radiation-induced polymerization, or a radical initiator.

Also, the manner of graft copolymerization in which the monomer compound represented by the aforementioned general formula (1) is graft-copolymerized to a base film comprising a fluorine-containing hydrocarbon polymer is not especially limited. For example, a monomer compound represented by the aforementioned general formula (1), which constitutes a side chain, is graft-copolymerized in the presence of the base film comprising the fluorine-containing hydrocarbon polymer, which constitutes the main chain, using thermopolymerization, radiation induced polymerization, or a radical initiator.

The obtained graft copolymer compound can be processed to manufacture a membrane by dissolving the graft copolymer in a solvent, casting the obtained solution on a support such as a glass plate, and then drying. The obtained film is, if necessary, processed by a hydrochloric acid solution or nitric acid solution, and then rinsed sufficiently with ion-exchanged water.

Examples of the solvent include an aromatic hydrocarbon solvent, an ether solvent, a ketone solvent, an amide solvent, a sulfone solvent, or a sulfoxide solvent. The sulfoxide solvent and the amide solvent are preferable among these solvents because of high solubility. The sulfoxide solvent is preferably dimethyl sulfoxide, for example. The amide solvent is preferably N,N-dimethylformamide, N,N-dimethylacetamide, or N-methyl-pyrrolidone, for example.

In order to improve the mechanical strength of the electrolyte membrane of the present invention, the electrolyte membrane may be irradiated with an electron beam or a radiation beam for crosslinking. It may also be impregnated in a porous film or sheet to make a complex, and fiber or pulp may be mixed to reinforce the film. Although the thickness of the electrolyte membrane is not especially limited, a thickness of 10 to 200 μm is preferable. A membrane whose thickness is less than 10 μm tends to have a declined strength, and a membrane whose thickness is greater than 200 μm tends to lack the characteristics of an electrochemical device because of increased membrane resistance. The membrane thickness can be controlled by the concentration of the solution or the thickness of the coating on the substrate.

The polymer electrolyte membrane according to the present invention can provide a sufficient proton conductivity even in a low-water-content state or a zero-water-content state without using additives unnecessary for the membrane components.

Therefore, the polymer electrolyte membrane according to the present invention, comprising a super strong-acidic group, is suitable as an ion exchange membrane in a polymer electrolyte fuel cell.

In the following, a fuel cell according to the present invention is described. The fuel cell according to the present invention can be manufactured by joining conductive substances as a catalyst and a collector to both surfaces of the polymer electrolyte membrane for fuel cells as mentioned above. The catalyst is not especially limited and various well-known substances can be used as long as they can activate an oxidation-reduction reaction with hydrogen or oxygen. However, fine particles of platinum are preferable. Fine particles of platinum are often carried by particulate or fibrous carbon, such as activated carbon or graphite. Regarding the conductive substance as a collector, although various well-known materials can be used, porous carbon non-woven fabric or carbon paper is preferable for efficiently transporting source gas to the catalyst. For joining the platinum fine particles or the carbon carrying the platinum fine particles to the porous carbon non-woven fabric or the carbon paper, and joining it to the polymer electrolyte membrane, well-known methods can be used.

Specifically, the fuel cell according to the present invention is PEFC. A stack formed by piling up a plurality of fuel cells is used as the fuel cell. And the aforementioned electrolyte membrane according to the present invention is used as the electrolyte membrane. A gas-supplying device that individually supplies fuel gas and oxidizing gas is connected to reactive electrodes on both sides that sandwich the electrolyte membrane via separators on the corresponding sides thereof. The fuel gas is preferably hydrogen gas, and the oxidizing gas is preferably air or oxygen gas.

The fuel cells according to the present invention have a structure where the electrolyte membrane is sandwiched on both sides thereof by the reactive electrodes, and an MEA sandwiched by diffusion layers is sandwiched on both sides thereof by separators. The reactive electrodes are not especially limited and conventional electrodes can be used. For example, a catalyst in which platinum or platinum alloy is dispersed on carbon powders can be used. The reactive electrodes can be formed by processing a membrane on the surface of the electrolyte membrane using the catalyst as it is or after mixing it with a binder, for example, such as an electrolyte solution of the invention. As the diffusion layers, a mixture of conventional carbon powders and hydrophobic polymer powders can be used, for example. The diffusion layers can also be formed including the electrolyte solution of the present invention. The separators may also employ conventional materials and forms. The separators are formed with a channel to which the gas-supplying device that supplies reactant gas and means for removing non-reacted reactant gas and generated water are connected.

The polymer electrolyte membrane according to the present invention shows sufficient proton conductivity even in a low-water-content state or zero-water-content state. Thus, in the fuel cell (PEFC) according to the present invention, system operation temperature can be increased and the need for a humidifier can be eliminated.

EXAMPLES

In the following, the present invention is described more specifically with reference to examples and comparative examples.

EXAMPLES

Monomer Synthesis

A monomer comprising a super strong-acidic group according to the present invention was synthesized by conducting the following reaction in Benzene/THF=1:1. The reaction temperatures and reaction time ware at 0° C. to room temperature, for 0.5 hour, and then at 70° C., for 6 hours.

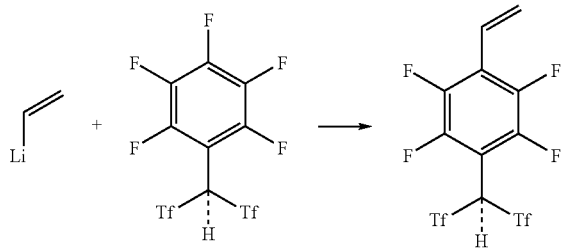

[Manufacturing of Graft Copolymer/Electrolyte Membrane]

The obtained monomer comprising a super strong-acidic group was directly graft-copolymerized to a base film comprising an ethylene-tetrafluoroethylene copolymer.

Comparative Example

Tf (trifluoromethane sulfonyl group ($-SO_2CF_3$)) as a super strong-acidic group was introduced to an ethylene-tetrafluoroethylene copolymer by the scheme shown in FIG. 1 in the same manner as in the present invention.

[Amount of Introduction of Super Strong-Acidic Group]

The amount of introduction of super strong-acidic groups per gram of the electrolyte membranes was compared between the example and the comparative example. Table 1 shows the results.

TABLE 1

|  | Amount of introduction [mmol/g] |
|---|---|
| Example | 4.85 |
| Comparative example | 0.23 |

As the result of Table 1 shows, about 20 times more introduction was confirmed in the present invention than in the comparative example. This is due to the fact that, since in the comparative example, the lithiation of the Br group does not proceed sufficiently in the first half of the reaction step, resulting in a small amount of reaction field in the latter half such that the amount of introduction of the intended super strong-acidic group cannot be increased.

[Conductivity]

The conductivity of the electrolyte membranes after introduction of the super strong-acidic groups was compared between the example and the comparative example. Table 2 shows the results. The measurement of the proton conductivity was conducted by cutting the membranes of the example and comparative example into a 5×40 mm section, and measuring the alternating-current impedance via the four terminal method. The measurement was conducted under conditions including temperatures of 80° C. and 120° C. with relative humidity of 100%, a constant current value of 0.005 mA, and the sweep frequency of 10 to 20000 Hz. The conductivity was measured using the obtained impedance and the distance between the membrane and the electrodes.

TABLE 2

|  | Conductivity [S/cm$^2$] |
|---|---|
| Example | $3.6 \times 10^{-3}$ |
| Comparative example | $2.8 \times 10^{-5}$ |

As the results of Table 2 show, the amount of introduction of super strong-acidic groups is larger in the present invention.

INDUSTRIAL APPLICABILITY

The highly proton-conductive electrolyte of the present invention can provide a sufficient proton conductivity with a high degree of dissociation even in a low humidity environment since a super strong-acidic group is used as for ion exchange. When the electrolyte of the graft copolymer according to the present invention is suitably used, for example, for the solid polymer electrolyte membrane of a polymer electrolyte fuel cell, power generation can be stably performed even in a low humidity environment. As a result, the fuel cell can be operated without humidification and at high temperatures, thereby allowing the battery to be reduced in size, provided with an anti-freeze property, and improved in efficiency, for example. The present invention will contribute a great deal to the industry.

Also, the highly proton-conductive electrolyte of the present invention can be suitably used for water electrolysis, common salt electrolysis, oxygen thickeners, humidity sensors, and gas sensors, for example, in addition to fuel cells.

The invention claimed is:

1. A graft copolymer in which a monomer represented by the general formula (1):

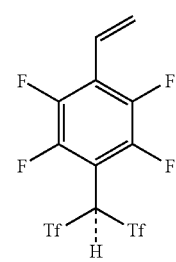

(1)

is graft-copolymerized to the main chain of a fluorine-containing hydrocarbon polymer, wherein Tf indicates a trifluoromethane sulfonyl group ($-SO_2CF_3$).

2. The graft copolymer according to claim 1 represented by the general formula (2):

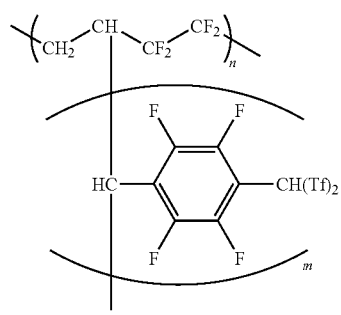

wherein the main chain of said fluorine-containing hydrocarbon polymer is an ethylene-tetrafluoroethylene copolymer, and Tf indicates a trifluoromethane sulfonyl group (—SO₂CF₃), n is not less than 10, and m is not less than 3.

3. A method for manufacturing a graft copolymer comprising graft-copolymerizing a monomer represented by the general formula (1):

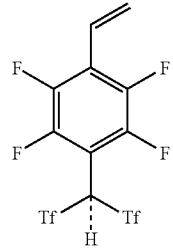

to a fluorine-containing hydrocarbon polymer, wherein Tf indicates a trifluoromethane sulfonyl group (—SO₂CF₃).

* * * * *